United States Patent [19]

Dinh et al.

[11] Patent Number: 5,599,352
[45] Date of Patent: Feb. 4, 1997

[54] METHOD OF MAKING A DRUG ELUTING STENT

[75] Inventors: Thomas Q. Dinh, Minnetonka; Ronald J. Tuch, Plymouth; Robert S. Schwartz, Rochester, all of Minn.

[73] Assignee: Medtronic, Inc., Minneapolis, Minn.

[21] Appl. No.: 306,785

[22] Filed: Sep. 15, 1994

Related U.S. Application Data

[63] Continuation-in-part of Ser. No. 79,222, Jun. 17, 1993, which is a continuation of Ser. No. 854,118, Mar. 19, 1992, abandoned.

[51] Int. Cl.$^6$ .................... A61F 2/06; A61F 2/04
[52] U.S. Cl. .................... 623/1; 623/12; 606/195; 600/36
[58] Field of Search .................... 623/1, 11, 12; 600/36; 606/191–200, 151–158; 604/8, 104

[56] References Cited

U.S. PATENT DOCUMENTS

| | | |
|---|---|---|
| 3,523,807 | 8/1970 | Gerendas . |
| 4,389,330 | 6/1983 | Tice et al. . |
| 4,464,317 | 8/1984 | Thies et al. . |
| 4,530,840 | 6/1985 | Tice et al. . |
| 4,540,573 | 9/1985 | Neurath . |
| 4,542,025 | 9/1985 | Tice et al. . |
| 4,548,736 | 10/1985 | Muller et al. .......... 252/315.1 |
| 4,600,652 | 7/1986 | Solomon et al. . |
| 4,622,244 | 11/1986 | Lapka et al. . |
| 4,642,242 | 2/1987 | Solomon et al. . |
| 4,675,189 | 6/1987 | Kent et al. . |
| 4,720,512 | 1/1988 | Hu et al. . |
| 4,886,062 | 12/1989 | Wiktor . |
| 4,897,268 | 1/1990 | Tice et al. . |
| 4,943,449 | 6/1990 | Aishima et al. . |
| 5,019,096 | 5/1991 | Fox, Jr. et al. .......... 623/1 |
| 5,092,841 | 3/1992 | Spears . |
| 5,116,962 | 5/1992 | Spears . |
| 5,141,516 | 8/1992 | Detweiler . |
| 5,223,420 | 6/1993 | Rabaud et al. . |
| 5,246,451 | 9/1993 | Trescony et al. . |

FOREIGN PATENT DOCUMENTS

| | | |
|---|---|---|
| 0166263 | 1/1986 | European Pat. Off. . |
| 0364787 | 9/1989 | European Pat. Off. . |
| 0366564 | 10/1989 | European Pat. Off. . |
| 0420541 | 4/1991 | European Pat. Off. . |
| 566245A1 | 10/1993 | European Pat. Off. . |
| 0604022 | 6/1994 | European Pat. Off. . |
| 0649637 | 4/1995 | European Pat. Off. . |
| WO9013332 | 11/1990 | WIPO . |
| WO9112779 | 9/1991 | WIPO . |
| 9117789 | 11/1991 | WIPO . |
| WO9222312 | 12/1992 | WIPO . |

OTHER PUBLICATIONS

"Effect of Balloon Inflation on Smooth Muscle Cell Proliferation in the Porcine Carotid Artery", by Webster Mark W. I. J. Am. Coll Cardiol. 15 (2) Feb. 1990:163A.

"Bioartificial polymeric materials obtained from blends of synthetic polymers with fibrin and collagen", by Soldani et al. Int'l J. of Artificial Organs 14(5) 1991:295–303.

"New Biolized Polymers for Cardiovascular Applications", Giusti et al. in Life Support Systems 3(suppl. 1.1) 1986:476–480.

"Restenosis After Balloon Angioplasty: A Practical Proliferative Model in Porcine Coronary Arteries", by Schwartz Robert S. et al. in Circulation 82(6) Dec. 1990:2190–2200.

"The Restenosis Paradigm Revisited: An Alternative Proposal for Cellular Mechanisms", Schwartz Robert S. in J. Am. Coll Cardiol 20(5) Nov. 1, 1992:1284–93.

(List continued on next page.)

*Primary Examiner*—Debra S. Brittingham
*Attorney, Agent, or Firm*—Daniel W. Latham; Harold R. Patton

[57] ABSTRACT

An intraluminal stent comprising fibrin and an elutable drug is capable of providing a treatment of restenosis.

13 Claims, 6 Drawing Sheets

OTHER PUBLICATIONS

"Restenosis and the Proportional Neointimal Response to Coronary Artery Injury: Results in a Porcine Model", Schwartz Robert S. in J. Am. Coll Cardiol, 19(2) Feb. 1992:267–74.

"Evaluation of Fibrin Seal in Animal Experiments", Haverich et al. in Thorac. Cardiovasc. Surgeon 30 1982:215–222.

"A Cascade Model for Restenosis: A Special Case of Atherosclerosis Progression", Libby et al. Circulation 86(6) Dec. 1992:III–47–III52.

"Use of Fibrin Film as a Carrier for Drug Delivery: In Vitro Drug Permeabilities of Fibrin Film", Miyazaki et al. Chem Pharm. Bull. 28(7) 1980:2261–2264.

"Polymeric Stenting in the Porcine Coronary Artery Model: Differential Outcome of Exogenous Fibrin Sleeves Versus Polyurethane–Coated Stents", by Holmes D. R. et al. J. Amer Coll Cardiol 24(2) Aug. 1994:525–31.

"Percutaneous Polymeric Stents in Porcine Coronary Arteries. Initial Experience with Polyethylene Terephthalate Stents", by Murphy R. G. et al. Circulation 86(5) Nov. 1992:1596–604.

"Seeding of Intravascular Stents with Genetically Engineered Endothelial Cells", Dichek, D. A. et al. Circulation 80 1989:1347–1353.

METHOD OF MAKING A DRUG ELUTING STENT

This is a continuation-in-part of Ser. No. 08/079,222 filed Jun. 17, 1993, now pending which is a continuation of Ser. No. 07/854,118 filed Mar. 19, 1992, now abandoned.

BACKGROUND OF THE INVENTION

This invention relates to a method for lessening restenosis of body lumens and to intraluminal stents having anti-thrombosis and anti-restenosis properties.

Restenosis is the reclosure of a peripheral or coronary artery following trauma to that artery caused by efforts to open a stenosed portion of the artery, such as, for example, by balloon dilation, ablation, atherectomy or laser treatment of the artery. For these angioplasty procedures, restenosis occurs at a rate of about 20–50% depending on the definition, vessel location, lesion length and a number of other morphological and clinical variables. Restenosis is believed to be a natural healing reaction to the injury of the arterial wall that is caused by angioplasty procedures. The healing reaction begins with the thrombotic mechanism at the site of the injury. The final result of the complex steps of the healing process can be intimal hyperplasia, the uncontrolled migration and proliferation of medial smooth muscle cells, combined with their extracellular matrix production, until the artery is again stenosed or occluded.

In an attempt to prevent restenosis, metallic intravascular stents have been permanently implanted in coronary or peripheral vessels. The stent is typically inserted by catheter into a vascular lumen and expanded into contact with the diseased portion of the arterial wall, thereby providing mechanical support for the lumen. However, it has been found that restenosis can still occur with such stents in place. Also, the stent itself can cause undesirable local thrombosis. To address the problem of thrombosis, persons receiving stents also receive extensive systemic treatment with anti-coagulant and antiplatelet drugs.

To address the restenosis problem, it has been proposed to provide stents which are seeded with endothelial cells (Dichek, D. A. et al Seeding of Intravascular Stents With Genetically Engineered Endothelial Cells; Circulation 1989; 80: 1347–1353). In that experiment, sheep endothelial cells that had undergone retrovirus-mediated gene transfer for either bacterial beta-galactosidase or human tissue-type plasminogen activator were seeded onto stainless steel stents and grown until the stents were covered. The cells were therefore able to be delivered to the vascular wall where they could provide therapeutic proteins. Other methods of providing therapeutic substances to the vascular wall by means of stents have also been proposed such as in international patent application WO 91/12779 "Intraluminal Drug Eluting Prosthesis" and international patent application WO 90/13332 "Stent With Sustained Drug Delivery". In those applications, it is suggested that antiplatelet agents, anticoagulant agents, antimicrobial agents, anti-inflammatory agents, antimetabolic agents and other drugs could be supplied in stents to reduce the incidence of restenosis. Further, other vasoreactive agents such as nitric oxide releasing agents could also be used.

In the vascular graft art, it has been noted that fibrin can be used to produce a biocompatible surface. For example, in an article by Soldani et at., "Bioartificial Polymeric Materials Obtained from Blends of Synthetic Polymers with Fibrin and Collagen" International Journal of Artificial Organs, Vol. 14, No. 5, 1991, polyurethane is combined with fibrinogen and cross-linked with thrombin and then made into vascular grafts. In vivo tests of the vascular grafts reported in the article indicated that the fibrin facilitated tissue ingrowth and was rapidly degraded and reabsorbed. Also, a published European Patent Application 0366564 applied for by Terumo Kabushiki Kaisha, Tokyo, Japan, discloses a medical device such as an artificial blood vessel, catheter or artificial internal organ which is made from a polymerized protein such as fibrin. The fibrin is said to be highly nonthrombogenic and tissue compatible and promotes the uniform propagation of cells that regenerate the intima. Also, in an article by Gusti et at., "New Biolized Polymers for Cardiovascular Applications", Life Support Systems, Vol. 3, Suppl. 1, 1986, "biolized" polymers were made by mixing synthetic polymers with fibrinogen and cross-linking them with thrombin to improve tissue ingrowth and neointima formation as the fibrin biodegrades. Also, in an article by Haverich et al., "Evaluation of Fibrin Seal in Animal Experiments", Thoracic Cardiovascular Surgeon, Vol. 30, No. 4, pp. 215–22, 1982, the authors report the successful sealing of vascular grafts with fibrin. In the copending application Ser. No. 08/079,222, it is disclosed that the problem of restenosis can be addressed by the use of fibrin in an intravascular stent. However, it would be desirable to provide a fibrin-based stent in which the stent also has a drug delivery capability that would allow drugs to be delivered locally to the site of a potential restenosis and then elute over a period of days to treat the blood vessel in the initial stages of restenosis and thereby prevent or limit restenosis.

SUMMARY OF THE INVENTION

These and other objects of the invention have been achieved by the present invention. An intraluminal stent comprising fibrin can provide a suitable device to administer drugs for treatment of restenosis. Fibrin is a naturally occurring bioabsorbable polymer of fibrinogen that arises during blood coagulation. As set forth above, providing fibrin at the site of treatment can provide a readily tolerated, bioabsorbable surface which will interact in a natural manner with the body's healing mechanism and reduce the prospect for the intimal hyperplasia that causes restenosis. Local administration of drugs via the fibrin matrix of the stent can further reduce the prospect of restenosis. A significant problem in this regard is how to provide a therapeutically useful amount of a substance in a relatively small fibrin stent.

To accomplish this while not affecting the strength of the overall fibrin stent structure, a first layer is applied to a stent body, the first layer incorporating a polymer and the therapeutic substance. The first layer is then overcoated with a second layer including fibrin which includes little or none of the therapeutic agent.

In one embodiment of the invention, a solution which includes a solvent, a polymer dissolved in the solvent and a therapeutic drug dispersed in the solvent is applied to the structural elements of the stent and then the solvent is evaporated. Fibrin can then be added over the coated structural elements. The inclusion of a polymer in intimate contact with a drug on the underlying stent structure allows the drug to be retained on the stent in a resilient matrix during expansion of the stent and also slows the administration of drug following implantation. The method can be applied whether the stent has a metallic or polymeric surface. The method is also an extremely simple method since it can be applied by simply immersing the stent into the solution or by spraying the solution onto the stent. The mount of drug to be included on the stent can be readily controlled by applying multiple thin coats of the solution while allowing it to dry between coats. The overall coating should be thin enough so that it will not significantly increase the profile of the stent for intravascular delivery by catheter. It is therefore preferably less than about 0.002 inch thick and most preferably less than 0.001 inch thick. The adhesion of the coating and the rate at which the drug is delivered can be controlled by the selection of an appropriate bioabsorbable or biostable polymer and by the ratio of drug to polymer in the solution. By this method, drugs such as glucocorticoids (e.g. dexamethasone, betamethasone), heparin, hirudin, tocopherol, angiopeptin, aspirin, ACE inhibitors, growth factors, oligonucleotides, and, more generally, antiplatelet agents, anticoagulant agents, antimitotic agents, antioxidants, antimetabolite agents, and anti-inflammatory agents can be applied to a stent, retained on a stent during expansion of the stent and elute the drug at a controlled rate. The release rate can be further controlled by varying the ratio of drug to polymer in the multiple layers.

In another embodiment of the invention, the polymer in the first layer is fibrin. The coating of polymer and drug on the stent is achieved by forming a first fibrin layer on the stent body by applying fibrinogen and thrombin to the stent; while the fibrin layer is polymerizing, applying a layer of a therapeutic substance to the polymerizing fibrin layer; and overcoating the therapeutic substance and fibrin with a second fibrin layer. Alternatively, the therapeutic substance can be dispersed in a solution of fibrinogen which is applied to a stent body and thrombin can then be added in order to effect polymerization of the fibrinogen and to provide a fibrin matrix to contain the therapeutic substance. According to this method the amount of therapeutic substance to be delivered by the stent can be controlled by employing multiple layers of fibrin and therapeutic substance.

BRIEF DESCRIPTION OF THE DRAWINGS

FIG. 4 is an elevational view of a stent and rigid tube into which the stent is inserted.

FIG. 5 is an elevational view of the tube of FIG. 4 into which a catheter balloon is inserted.

FIG. 6 is partial sectional view of the tube of FIG. 5 with included stent and catheter.

FIG. 7 is a partial sectional view of the tube of FIG. 6 to which fibrin has been added.

FIG. 8 is a partial sectional view of the tube of FIG. 7 in which the balloon has been expanded.

FIG. 9 is an elevational view of the resulting stent being removed from the tube of FIG. 8.

FIG. 10 is an elevational view of the completed stent mounted on the balloon of a catheter.

DETAILED DESCRIPTION OF THE INVENTION

Figure 1:
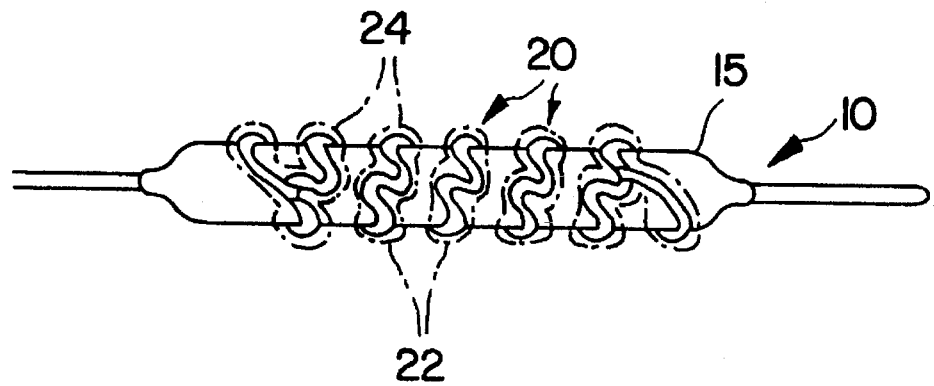
FIG. 1 is an elevational view of a balloon catheter with a metallic stent including a fibrin coating according to the present invention.

The present invention provides a stent comprising fibrin. The term "fibrin" herein means the naturally occurring polymer of fibrinogen that arises during blood coagulation.

Blood coagulation generally requires the participation of several plasma protein coagulation factors: factors XII, XI, IX, X, VIII, VII, V, XIII, prothrombin, and fibrinogen, in addition to tissue factor (factor III), kallikrein, high molecular weight kininogen, $Ca^{+2}$, and phospholipid. The final event is the formation of an insoluble, cross-linked polymer, fibrin, generated by the action of thrombin on fibrinogen. Fibrinogen has three pairs of polypeptide chains (ALPHA 2—BETA 2—GAMMA 2) covalently linked by disulfide bonds with a total molecular weight of about 340,000. Fibrinogen is converted to fibrin through proteolysis by thrombin. An activation peptide, fibrinopeptide A (human) is cleaved from the amino-terminus of each ALPHA chain; fibrinopeptide B (human) from the amino-terminus of each BETA chain. The resulting monomer spontaneously polymerizes to a fibrin gel. Further stabilization of the fibrin polymer to an insoluble, mechanically strong form, requires cross-linking by factor XIII. Factor XIII is converted to XIIIa by thrombin in the presence of $Ca^{+2}$. XIIIa cross-links the GAMMA chains of fibrin by transglutaminase activity, forming EPSILON-(GAMMA-glutamyl) lysine cross-links. The ALPHA chains of fibrin also may be secondarily cross-linked by transamidation.

Since fibrin blood clots are naturally subject to fibrinolysis as part of the body's repair mechanism, implanted fibrin can be rapidly biodegraded. Plasminogen is a circulating plasma protein that is adsorbed onto the surface of the fibrin polymer. The adsorbed plasminogen is converted to plasmin by plasminogen activator released from the vascular endothelium. The plasmin will then break down the fibrin into a collection of soluble peptide fragments.

Methods for making fibrin and forming it into implantable devices are well known as set forth in the following patents and published applications which are hereby incorporated by reference. In U.S. Pat. No. 4,548,736 issued to Muller et al., fibrin is clotted by contacting fibrinogen with a fibrinogen-coagulating protein such as thrombin, reptilase or ancrod. Preferably, the fibrin in the fibrin-containing stent of the present invention has Factor XIII and calcium present during clotting, as described in U.S. Pat. No. 3,523,807 issued to Gerendas, or as described in published European Patent Application 0366564, in order to improve the mechanical properties and biostability of the implanted device. Also preferably, the fibrinogen and thrombin used to make fibrin in the present invention are from the same animal or human species as that in which the stent of the present invention will be implanted in order to avoid cross-species immune reactions. The resulting fibrin can also be subjected to heat treatment at about 150° C. for 2 hours in order to reduce or eliminate antigenicity. In the Muller patent, the fibrin product is in the form of a fine fibrin film produced by casting the combined fibrinogen and thrombin in a film and then removing moisture from the film osmotically through a moisture permeable membrane. In the European Patent Application 0366564, a substrate (preferably having high porosity or high affinity for either thrombin or fibrinogen) is contacted with a fibrinogen solution and with a thrombin solution. The result is a fibrin layer formed by polymerization of fibrinogen on the surface of the device. Multiple layers of fibrin applied by this method could provide a fibrin layer of any desired thickness. Or, as in the Gerendas patent, the fibrin can first be clotted and then ground into a powder which is mixed with water and stamped into a desired shape in a heated mold. Increased stability can also be achieved in the shaped fibrin by contacting the fibrin with a fixing agent such as glutaraldehyde or formaldehyde. These and other methods known by those skilled in the art for making and forming fibrin may be used in the present invention.

Preferably, the fibrinogen used to make the fibrin is a bacteria-free and virus-free fibrinogen such as that described in U.S. Pat. No. 4,540,573 to Neurath et al which is hereby incorporated by reference. The fibrinogen is used in solution with a concentration between about 10 and 50 mg/ml and with a pH of about 5.8–9.0 and with an ionic strength of about 0.05 to 0.45. The fibrinogen solution also typically contains proteins and enzymes such as albumin, fibronectin (0–300 µg per ml fibrinogen), Factor XIII (0–20 µg per ml fibrinogen), plasminogen (0–210 µg per ml fibrinogen), antiplasmin (0–61 µg per ml fibrinogen) and Antithrombin III (0–150 µg per ml fibrinogen). The thrombin solution added to make the fibrin is typically at a concentration of 1 to 120 NIH units/ml with a preferred concentration of calcium ions between about 0.02 and 0.2M.

Preferably the coagulating effect of any residual coagulation protein in the fibrin should be neutralized before employing it in the stent of the present invention in order to prevent clotting at the fibrin interface with blood after stent implantation. This can be accomplished, for example, by treating the fibrin with irreversible coagulation inhibitor compounds or heat after polymerization. For example, hirudin or D-phenylalanyl-propyl-arginine chloromethyl ketone (PPACK) could be used. Anti-coagulants such as heparin can also be added to reduce the possibility of further coagulation. To ensure the effectiveness of the treatment with coagulation inhibitor or anti-coagulant it may be desirable to apply such materials within 30 minutes before implantation of the device.

Polymeric materials can also be intermixed in a blend or co-polymer with the fibrin to produce a material with the desired properties of fibrin with improved structural strength. For example, the polyurethane material described in the article by Soldani et at., "Bioartificial Polymeric Materials Obtained from Blends of Synthetic Polymers with Fibrin and Collagen" International Journal of Artificial Organs, Vol. 14, No. 5, 1991, which is incorporated herein by reference, could be sprayed onto a suitable stent structure. Suitable polymers could also be biodegradable polymers such as polyphosphate ester, polyhydroxybutyrate valerate, polyhydroxybutyrate-co-hydroxyvalerate and the like.

Also, the stent could be made with a porous polymeric sheet material into which fibrin is incorporated. Such a sheet material could be made, for example, as a polyurethane by dissolving a polyether urethane in an organic solvent such as methyl-2-pyrrolidone; mixing into the resulting polyurethane solution a crystalline, particulate material like salt or sugar that is not soluble in the solvent; casting the solution with particulate material into a thin film; and then applying a second solvent, such as water, to dissolve and remove the particulate material, thereby leaving a porous sheet. The porous sheet could then be placed into a fibrinogen solution in order to fill the pores with fibrinogen followed by application of a solution of thrombin and fibrinogen to the surface of the sheet to establish a fibrin matrix that occupies both the surface of the sheet and the pores of the sheet. Preferably, a vacuum would be pulled on the sheet to insure that the fibrinogen applied to the sheet is received into the pores.

The shape for the fibrin can be provided by molding processes. For example, the mixture can be formed into a stent having essentially the same shape as the stent shown in U.S. Pat. No. 4,886,062 issued to Wiktor. Unlike the method for making the stent disclosed in Wiktor which is wound from a wire, the stent made with fibrin can be directly molded into the desired open-ended tubular shape.

In U.S. Pat. No. 4,548,736 issued to Muller et al., a dense fibrin composition is disclosed which can be a bioabsorbable matrix for delivery of drugs to a patient. Such a fibrin composition can also be used in the present invention by incorporating a drug or other therapeutic substance useful in diagnosis or treatment of body lumens to the fibrin provided on the stent. The drug, fibrin and stent can then be delivered to the portion of the body lumen to be treated where the drug may elute to affect the course of restenosis in surrounding luminal tissue. Examples of drugs that are thought to be useful in the treatment of restenosis are disclosed in published international patent application WO 91/12779 "Intraluminal Drug Eluting Prosthesis" which is incorporated herein by reference. Therefore, useful drugs for treatment of restenosis and drugs that can be incorporated in the fibrin and used in the present invention can include drugs such as anticoagulant drugs, antiplatelet drugs, antimetabolite drugs, anti-inflammatory drugs and antimitotic drugs. Further, other vasoreactive agents such as nitric oxide releasing agents could also be used. Such therapeutic substances can also be microencapsulated prior to their inclusion in the fibrin. The micro-capsules then control the rate at which the therapeutic substance is provided to the blood stream or the body lumen. This avoids the necessity for dehydrating the fibrin as set forth in Muller et al., since a dense fibrin structure would not be required to contain the therapeutic substance and limit the rate of delivery from the fibrin. For example, a suitable fibrin matrix for drug delivery can be made by adjusting the pH of the fibrinogen to below about pH 6.7 in a saline solution to prevent precipitation (e.g., NACl, CaCl, etc.), adding the microcapsules, treating the fibrinogen with thrombin and mechanically compressing the resulting fibrin into a thin film. The microcapsules which are suitable for use in this invention are well known. For example, the disclosures of U.S. Pat. Nos. 4,897,268, 4,675, 189; 4,542,025; 4,530,840; 4,389,330; 4,622,244; 4,464, 317; and 4,943,449 could be used and are incorporated herein by reference. Alternatively, in a method similar to that disclosed in U.S. Pat. No. 4,548,736 issued to Muller et al., a dense fibrin composition suitable for drug delivery can be made without the use of microcapsules by adding the drug directly to the fibrin followed by compression of the fibrin into a sufficiently dense matrix that a desired elution rate for the drug is achieved. In yet another method for incorporating drugs which allows the drug to elute at a controlled rate, a solution which includes a solvent, a polymer dissolved in the solvent and a therapeutic drug dispersed in the solvent is applied to the structural elements of the stent and then the solvent is evaporated. Fibrin can then be added over the coated structural elements in an adherent layer. The inclusion of a polymer in intimate contact with a drug on the underlying stent structure allows the drug to be retained on the stent in a resilient matrix during expansion of the stent and also slows the administration of drug following implantation. The method can be applied whether the stent has a metallic or polymeric surface. The method is also an extremely simple method since it can be applied by simply immersing the stent into the solution or by spraying the solution onto the stent. The amount of drug to be included on the stent can be readily controlled by applying multiple thin coats of the solution while allowing it to dry between coats. The overall coating should be thin enough so that it will not significantly increase the profile of the stent for intravascular delivery by catheter. It is therefore preferably less than about 0.002 inch thick and most preferably less than 0.001 inch thick. The adhesion of the coating and the rate at which the drug is delivered can be controlled by the selection of an appropriate bioabsorbable or biostable polymer and by the ratio of drug to polymer in the solution. By this method, drugs such as glucocorticoids (e.g. dexamethasone, betamethasone), heparin, hirudin, tocopherol, angiopeptin, aspirin, ACE inhibitors, growth factors, oligonucleotides, and, more generally, antiplatelet agents, anticoagulant agents, antimitotic agents, antioxidants, antimetabolite agents, and anti-inflammatory agents can be applied to a stent, retained on a stent during expansion of the stent and elute the drug at a controlled rate. The release rate can be further controlled by varying the ratio of drug to polymer in the multiple layers. For example, a higher drug-to-polymer ratio in the outer layers than in the inner layers would result in a higher early dose which would decrease over time. Examples of some suitable combinations of polymer, solvent and therapeutic substance are set forth in Table 1 below.

TABLE 1

| POLYMER | SOLVENT | THERAPEUTIC SUBSTANCE |
| --- | --- | --- |
| poly(L-lactic acid) | chloroform | dexamethasone |
| poly(lactic acid-co-glycolic acid) | acetone | dexamethasone |
| polyether urethane | N-methyl pyrrolidone | tocopherol (vitamin E) |
| silicone adhesive | xylene | dexamethasone phosphate |
| poly(hydroxy-butyrate-co-hydroxyvalerate) | dichloro-methane | aspirin |

The polymer used can be a bioabsorbable or biostable polymer. Suitable bioabsorbable polymers include poly(L-lactic acid), poly(lactide-co-glycolide) and poly(hydroxybutyrate-co-valerate). Suitable biostable polymers include silicones, polyurethanes, polyesters, vinyl homopolymers and copolymers, acrylate homopolymers and copolymers, polyethers and cellulosics. A typical ratio of drug to dissolved polymer in the solution can vary widely (e.g. in the range of about 10:1 to 1:100). The fibrin is applied by molding a polymerization mixture of fibrinogen and thrombin onto the composite as described herein.

In another embodiment of the invention, the coating of polymer and drug on the stent is achieved by forming a first fibrin layer on the stent body which incorporates the therapeutic substance and then applying a second layer of fibrin. One way this may be accomplished is by applying fibrinogen and thrombin to the stent; while the fibrin layer is polymerizing, applying a layer of a therapeutic substance to the to the polymerizing fibrin layer; and then overcoating the therapeutic substance and fibrin with a second fibrin layer. According to this method the amount of therapeutic substance to be delivered by the stent can be controlled by employing multiple layers of fibrin and therapeutic substance. For example, to incorporate dexamethasone into a stent the stent body is first wetted with a fibrinogen solution (e.g. 5 mg/ml) and then wetted with a thrombin solution (e.g. 12 NIH units/ml) in order to form fibrin on the stent surface. After about 2–3 minutes, while the surface is still tacky, apply a known concentration of dexamethasone powder to the tacky fibrin. This can be accomplished by any number of methods, including rolling or spraying the powder onto the fibrin. After about 5 minutes at room temperature, the dexamethasone-coated stent is ready to be coated with the second layer of fibrin. This can be accomplished in a mold as described below. In yet another way this embodiment of the invention can be carried out, a water dispersible (or soluble) therapeutic substance is dispersed in the fibrinogen solution and this solution is applied to a stent body. Thrombin is added to polymerize the fibrinogen on the stent body and thereby produce a fibrin with a therapeutic substance incorporated in the fibrin matrix. The first fibrin layer can then be provided with the second fibrin coating.

Figure 2:
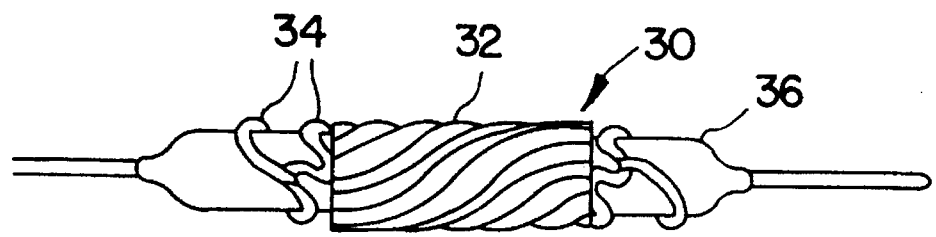
FIG. 2 is an elevational view of a balloon catheter with a metallic stent including a fibrin film according to the present invention.

The term "stent" herein means any device which when placed into contact with a site in the wall of a lumen to be treated, will also place fibrin at the lumen wall and retain it at the lumen wall. This can include especially devices delivered percutaneously to treat coronary artery occlusions and to seal dissections or aneurysms of splenic, carotid, iliac and popliteal vessels. The stent can also have underlying polymeric or metallic structural elements onto which the fibrin is applied or the stent can be a composite of fibrin intermixed with a polymer. For example, a deformable metal wire stent such as that disclosed in U.S. Pat. No. 4,886,062 issued to Wiktor could be coated with fibrin as set forth above in one or more coats (i.e. polymerization of fibrin on the metal framework by application of a fibrinogen solution and a solution of a fibrinogen-coagulating protein) or provided with an attached fibrin preform such as an encircling film of fibrin made as set forth above (i.e. a cast film as set forth in the Muller et al. patent). The stent and fibrin could then be placed onto the balloon at a distal end of a balloon catheter and delivered by conventional percutaneous means (e.g. as in an angioplasty procedure) to the site of the restriction or closure to be treated where it would then be expanded into contact with the body lumen by inflating the balloon. The catheter can then be withdrawn, leaving the fibrin stent of the present invention in place at the treatment site. The stent may therefore provide both a supporting structure for the lumen at the site of treatment and also a structure supporting the secure placement of fibrin at the lumen wall. FIG. 1 shows a stent having this general construction in place on a balloon catheter. A catheter 10 has a balloon 15 upon which a stent 20 has been placed, the stent 20 having a deformable metal portion 22 and a fibrin coating 24 thereon. FIG. 2 shows an alternative stent 30 in which a fibrin film 32 has been affixed to the underlying metallic framework 34 by affixing it to the stent 30 by e.g. wrapping the film 32 around the framework 34 and securing the film 32 to the framework 34 (i.e. the film is usually sufficiently tacky to adhere itself to the framework but an adhesive material could also be used if needed) so that the film 32 will stay on the balloon 36 and framework 34 until it is delivered to the site of treatment. The film 32 is preferably wrapped over the framework 34 with folds or wrinkles that will allow the stent 30 to be readily expanded into contact with the wall of the lumen to be treated.

Figure 3:
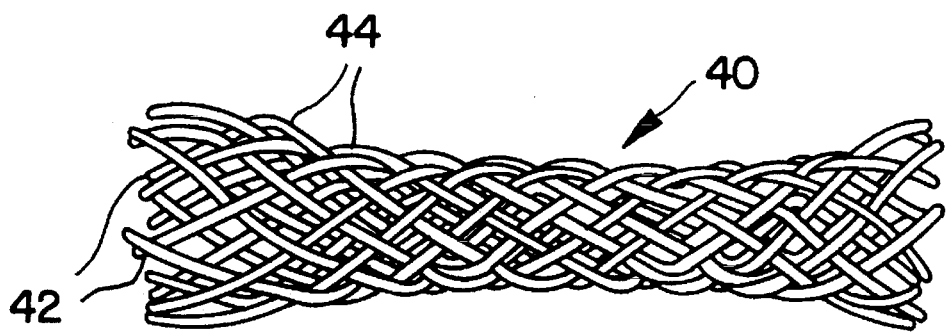
FIG. 3 is an elevational view of a polymeric stent incorporating fibrin according to the present invention.
Figure 4:
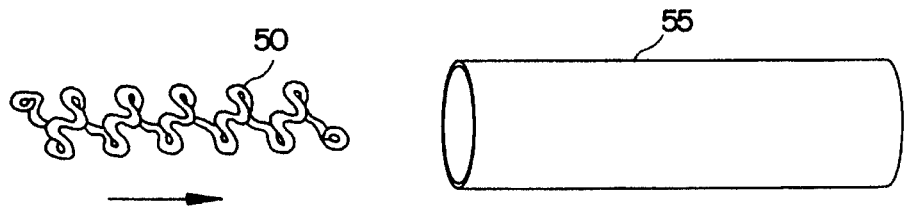
FIGS. 4–10 illustrate a method of making a stent according to the present invention.
Figure 5:
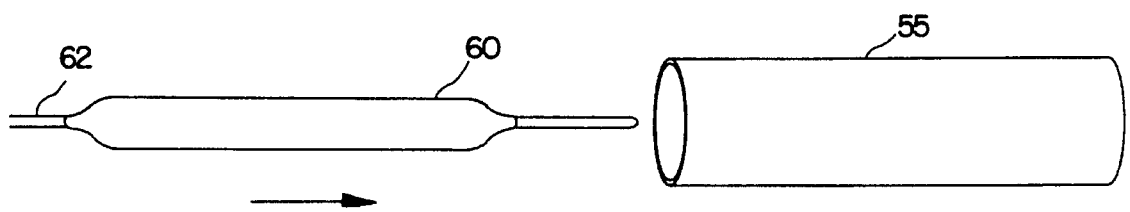
Figure 6:
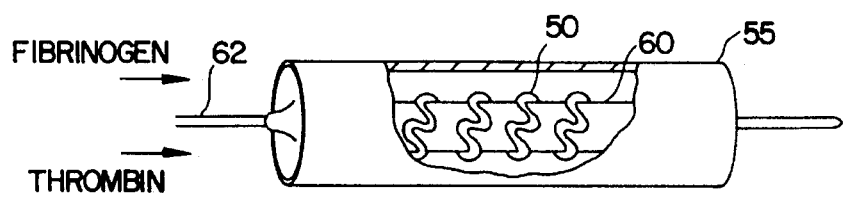
Figure 7:
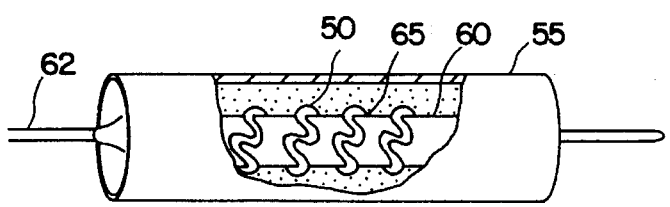
Figure 8:
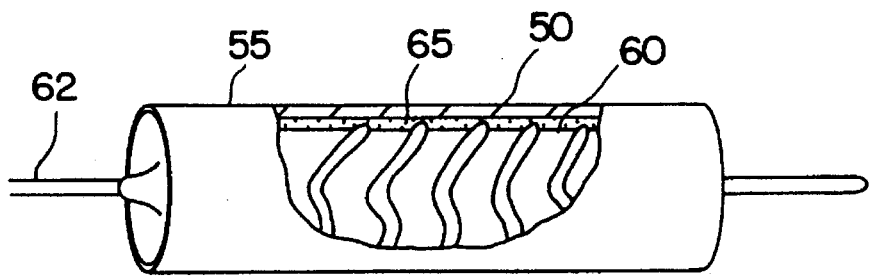
Figure 9:
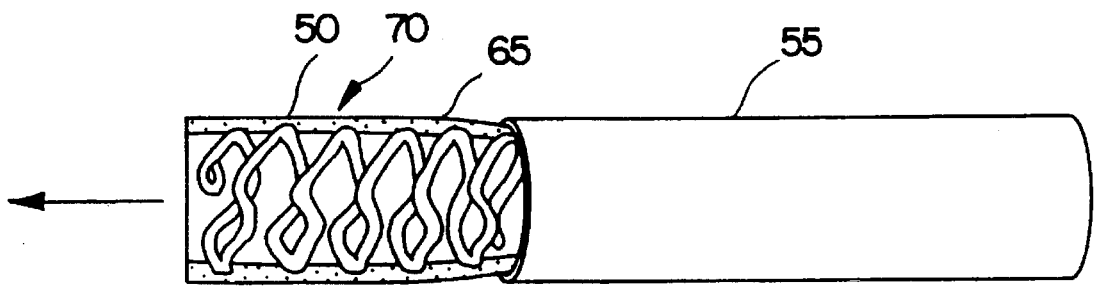
Figure 10:
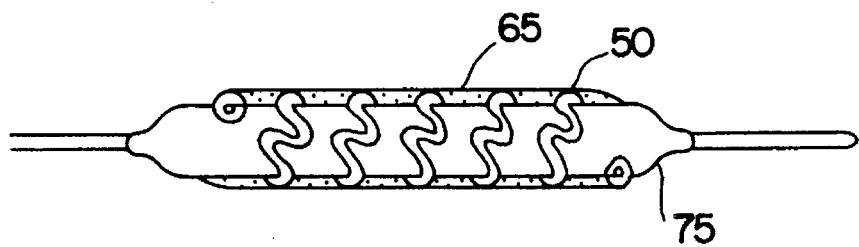

Also, for example, a self-expanding stent of resilient polymeric material such as that disclosed in published international patent application WO 91/12779 "Intraluminal Drug Eluting Prosthesis" could be used in which fibrin is coated onto the stent or incorporated within the polymeric material of the stent. A stent of this general configuration is shown in FIG. 3. The stent 40 has a first set of filaments 42 which are helically wound in one direction and a second set of filaments 44 which are helically wound in a second direction. Any or all of these filaments 42, 44 could be fibrin and/or a blend of fibrin with another polymer. The combination of fibrin with another polymer may be preferred to provide improved mechanical properties and manufacturability for the individual filaments 42, 44. A suitable material for fibrin-containing filaments 42, 44 is the crosslinked blend of polyurethane and fibrin used as a vascular graft material in the article by Soldani et al., "Bioartificial Polymeric Materials Obtained from Blends of Synthetic Polymers with Fibrin and Collagen" International Journal of Artificial Organs, Vol. 14, No. 5, 1991, which is incorporated herein by reference. Other biostable or bioerodeable polymers could also be used. A fibrin-containing stent of this configuration can be affixed to the distal end of a catheter in a longitudinally stretched condition which causes the stent to decrease in diameter. The stent is then delivered through the body lumen on the catheter to the treatment site where the stent is released from the catheter to allow it to expand into contact with the lumen wall. A specialized device for deploying such a stent is disclosed in U.S. Pat. No. 5,192, 297 issued to Hull. It will be apparent to those skilled in the art that other self-expanding stent designs (such as resilient metal stent designs) could also be used with fibrin either incorporated in the material of the underlying structure of the stent or filmed onto the underlying structure of the stent.

A preferred method of making a stent according to the present invention is as set forth in FIGS. 4–10. A stent 50 of the type disclosed in U.S. Pat. No. 4,886,062 issued to Wiktor is inserted into a tube 55 which is preferably made from a rigid material and which has an inside diameter which is large enough to accommodate an unexpanded PTCA balloon but which is smaller than a fully inflated PTCA balloon. A PTCA balloon 60 attached to a catheter 62 and inflation device (not shown) is inserted into the stent 50 and tube 55. Fibrinogen at a pH of about 6.5, suspended in a saline solution, and thrombin are inserted into the tube 55 around the deflated balloon 60 and stent 50. The amount of thrombin added is not critical but preferably will polymerize the fibrinogen to fibrin 65 in about 5 minutes. After polymerization, the fibrin is allowed to crosslink for at least an hour, preferably several hours. The balloon 60 is then inflated to compress the fibrin 65 between the balloon 60 and tube 55. The balloon 60 is then deflated and removed from the tube 55. The resulting fibrin stent 70 includes the stent 50 embedded in a very thin elastic film of fibrin 65. The fibrin stent 70 may then be removed from the tube 55 and washed in a buffered saline solution.

Further processing of the fibrin stent can also be undertaken to neutralize thrombin with PPACK or hirudin; to add anticoagulants such as heparin; to further facilitate crosslinking by incubation at body temperature in a biological buffer such as a solution of blood serum buffered by 4-(2-Hydroxyethyl)-1-piperazineethanesulfonic acid (HEPES); or to add plasticizers such as glycerol. The resulting fibrin stent can then be placed over a balloon, and secured onto the balloon by crimping. The stent can then be delivered transluminally and expanded into place in the body lumen by conventional procedures.

Preferably, heparin is incorporated into the stent prior to implantation in an amount effective to prevent or limit thrombosis. For example, the fibrin stent can be immersed in a solution of heparin within 10–30 minutes prior to implantation. The heparin immersion procedure can be conducted in a heparin solution having a concentration of about 1000–25,000 heparin units/ml. It may also be desirable to incorporate heparin into the fibrin matrix before it is completely polymerized. For example, after the fibrinogen and thrombin have been combined and the resulting fibrin has been shaped but within two hours of combining the fibrinogen and thrombin, the fibrin is immersed in a solution of heparin. Since the fibrin polymerization is largely complete at this point, the fibrin can be immersed in heparin solution containing up to about 20,000 units/ml of heparin without damaging the integrity of the fibrin structure. Immersion times will depend on the concentration of the heparin solution and the concentration of heparin desired in the fibrin. However, preferably, in a solution of heparin having a concentration of about 10,000–20,000 units/ml of heparin, an immersion time of about 12–24 hours may be used. In yet another method for incorporation of heparin in the fibrin, the heparin can be included in the fibrinogen or in the initial mixture of fibrinogen and thrombin so long as the ratio of heparin to fibrinogen is such that the presence of the heparin does not lead to a weak fibrin film. Typically, less than about 50–500 units of heparin can be used in a stent which includes 0.003–0.006 grams of fibrin. In yet another method for incorporating heparin into the fibrin, powdered heparin can be dusted onto the stent during the polymerization process and additional thrombin and fibrinogen can then be applied as a coating over the heparin.

The metal stent portion mentioned above may be eliminated to make a fibrin tube which can be placed on a balloon catheter and expanded into place in a body lumen. The absence of permanently implanted metal elements would allow the entire stent to biodegrade as healing is completed in the body lumen. In order to achieve sufficient structural support for a stent without a metal structure, it may be desirable to form supporting elements from elastin or elastin/fibrin/collagen/fibronectin as replacements for the metal supporting elements. If desired, fibrin glue or fibrinogen can also be applied to the exterior of the fibrin tube immediately prior to placing it into the blood vessel in order to improve its adhesion to the vessel wall.

Figure 11:
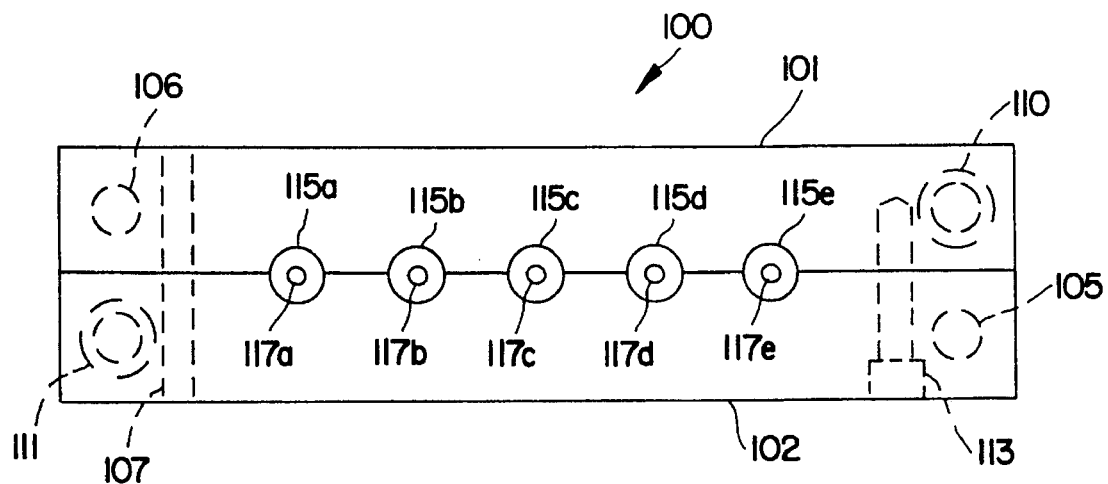
FIG. 11 is a top plan view of a multi-cavity mold for making a stent according to the invention.
Figure 12:
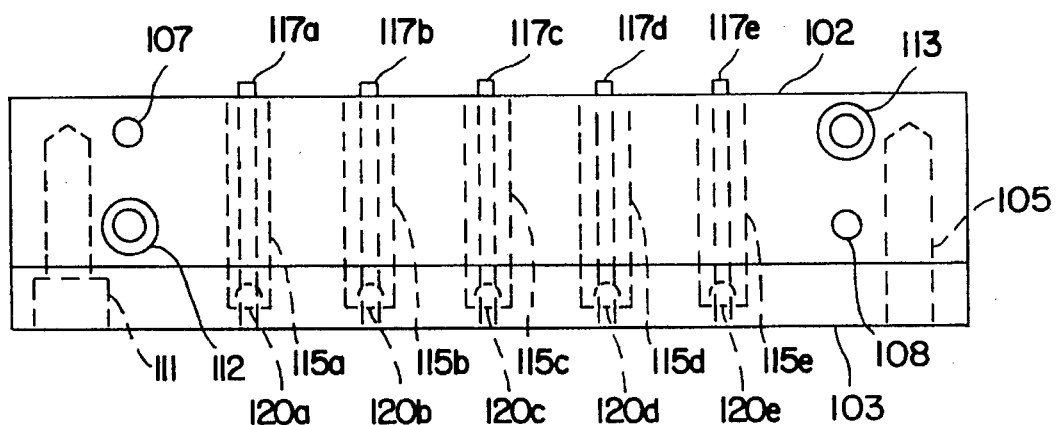
FIG. 12 is an elevational view of the mold of FIG. 11.
Figure 13:
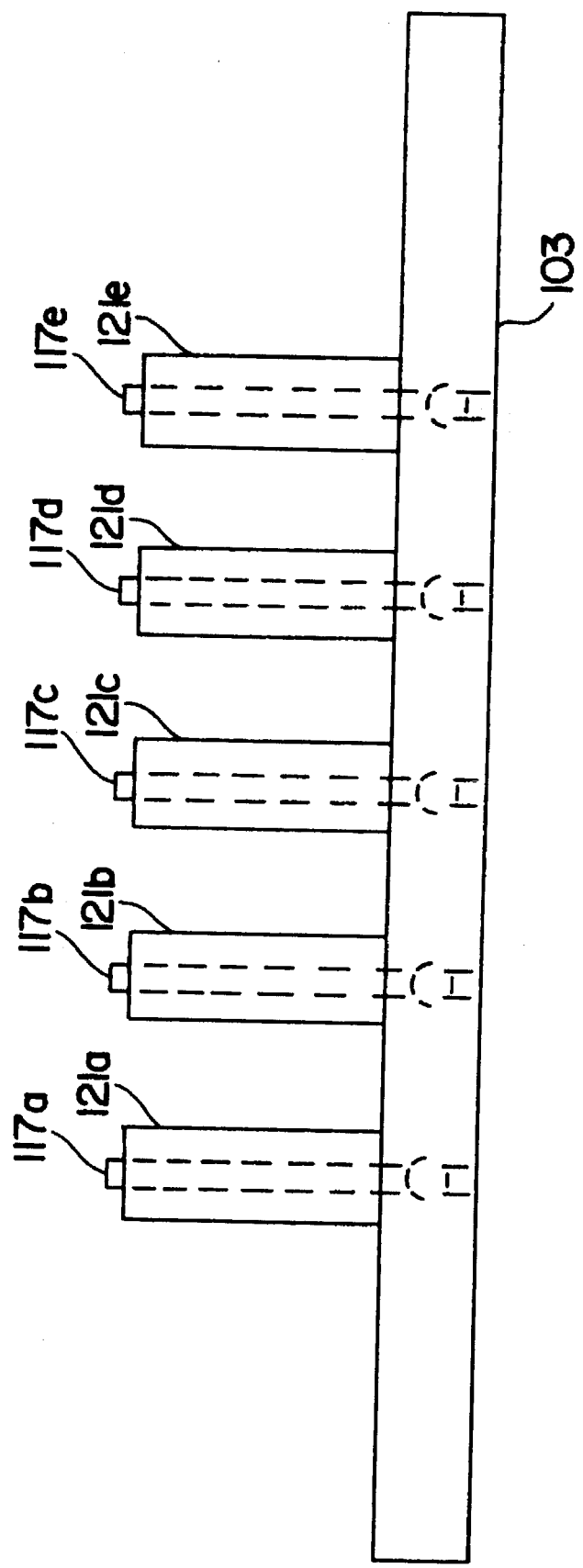
FIG. 13 is an elevational view of the mold of FIG. 12 with the top mold halves removed.

In yet another method for making the fibrin stent, the fibrin can be polymerized in a multi-cavity mold such as that shown in FIGS. 11 and 12. The mold 100 is a three piece mold consisting of first and second mold halves 101, 102 and mold base 103. A series of pins 105–108 and screws 110–113 secure the mold pieces 101–103 together. As assembled, the mold halves 101, 102 define five mold cavities 115a–e. Centrally located within each of the mold cavities 115a–e is a corresponding pin 117a–e which is retained in the mold base 103. In the mold base 103 is a series of laterally extending air passageways 120a–e which communicate with the cavities 115a–e to allow complete filling of the mold cavity. The molding surfaces are coated with a polymeric slip coating such as PTFE to permit the piece parts to be removed from the mold cavities after curing. FIG. 13 shows the mold base 103 of FIG. 12 after the mold halves 101, 102 have been removed following the molding operation. Pins 117a–e are shown surrounded by the molded fibrin 121a–e.

Figure 14:
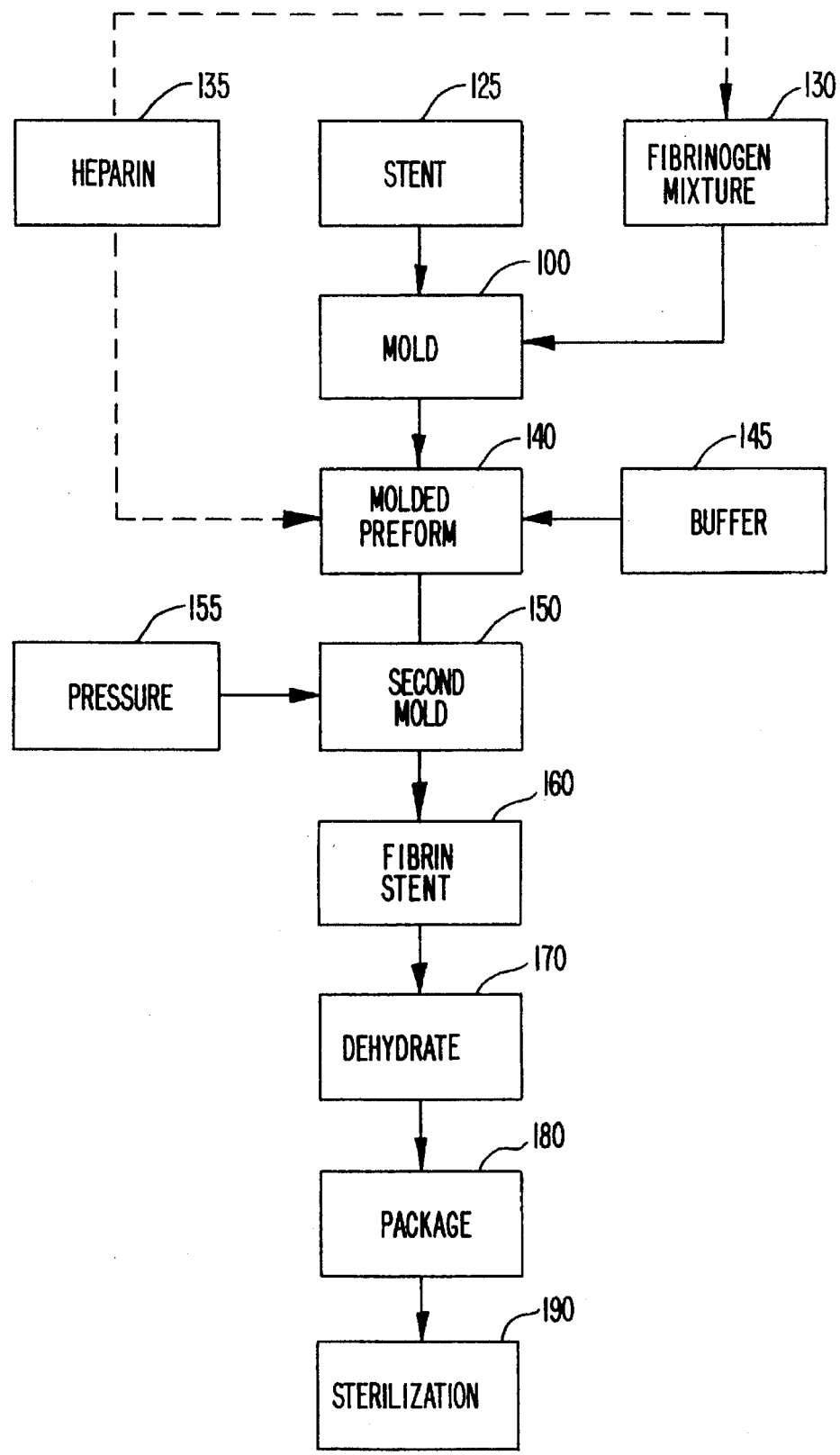
FIG. 14 is a flowchart of a process for making a fibrin stent using the multicavity mold of FIGS. 11 and 12.

Now referring also to FIG. 14, in operation, a stent 125 is placed into the mold 100 into one of the mold cavities 115a such that the pin 117a occupies the hollow center of the stent 125. A fibrinogen mixture with thrombin 130 is made by metering the fibrinogen solution and thrombin solution into a sterile syringe and then moving the plunger of the syringe to mix the solutions. For example, 0.5 ml of a fibrinogen solution having a concentration of 26 mg/ml can be mixed with 0.125 ml of a thrombin solution having a concentration of 12 NIH units/ml. The mixture 130 is then injected into the bottom of the cavity 115a of the mold 100 to fill the cavity 115a and encompass the stent 125. The mixture 130 is then allowed to cure. With the mixture indicated above, the curing interval should be at least two hours. Once the mixture 130 has clotted, sterile water may be applied by spraying onto the mold 100 to prevent the fibrin from drying out. When cured, the molded preform 140 comprising the stent 125 and the cured mixture 130 is removed from the mold 100 by removing the mold base 103 and pulling the molded preform 140 from the pin 117a. Since the pin 117 is coated with PTFE, the cured mixture 130 does not adhere to the pin 117a and the molded preform 140 can be removed by carefully pushing the preform from the bottom of pin 117a using a plastic tweezers. If required, excess fibrin can be trimmed from the preform 140 at this point or trimming can take place at a later stage of processing where the fibrin is stronger. The preform 140 can then be further crosslinked by treating it in a buffer solution 145 which may optionally contain crosslinking agents such as Factor XIIIa. For example, the buffer 145 could be a tris buffer with a pH of 7.4 with the preform 140 immersed in the tris buffer for at least five hours. Preferably, a solution of heparin 135 is also included in the mixture 130. The mixture 130 with heparin 135 is then injected into the cavity 115a of the mold 100 and allowed to cure. Alternatively, immediately after the preform 140 is removed from the mold 100, the preform 140 can be immersed in a heparin solution. After crosslinking, the preform 140 undergoes an additional molding stage in a cavity of a second mold 150 in which pressure 155 is applied to provide the final form of the fibrin stent 160. For example, the mold can simply be a polycarbonate tube and the preform 140 can be placed over the balloon of a balloon catheter and into the tube. The balloon is then slowly inflated causing the preform 140 to be pressed against the sides of the tube. The effect of the expansion and pressure on the fibrin is to stretch it and thin it because of the viscoelastic properties of the fibrin. Because fibrin is such a fragile material, it is important to control the expansion by slow expansion to prevent the fibrin from tearing and also to provide a stent with the proper dimensions for expansion in vivo without tearing. For example, the preform 140 may have an internal diameter of about 2.7 mm and may be placed on a 3.5 mm balloon and into a mold 150 having a 3.4 mm internal diameter. The balloon can then be expanded slowly at one atmosphere increments until a pressure of about six atmospheres is achieved. Pressure 155 is then typically maintained on the fibrin stent 160 inside the second mold 150 for a short period of time in order to set the fibrin stent 160 into its final shape. Typically thirty minutes at six atmospheres of pressure is sufficient. Upon release of pressure in the balloon, the balloon and fibrin stent 160 can be withdrawn from the mold 150. If the fibrin stent 160 is to be packaged and shipped dry, it can then be dehydrated 170 by well known methods such as air drying, ethanol dehydration or lyophilization and packaged 180 for storage and use. Typically, after packaging 180, the fibrin stent 160 is sterilized 190 by gamma or E-beam sterilization. It will be readily appreciated that a fibrin stent with an attached metallic framework can be readily provided by this molding method.

Sterilization of the fibrin stent can be accomplished by starting with sterile, virus-free materials and manufacturing the device under sterile processing conditions. The sterile processing conditions include manufacturing the device under standard clean room conditions and ending the manufacturing process with a final sterilization step. The final sterilization step would expose the packaged device to radiation, preferably gamma radiation, at a level sufficient to cause disruption of microorganism DNA. This can be accomplished at an approximately 2.5 MRad gamma ray dosage. A suitable gamma ray source can be e.g. cobalt-60 or cesium-137. Another suitable form of radiation can be electron beam radiation. The packaged device configuration at irradiation can be either dry or wet—i.e. with the fibrin stent in the package in a dehydrated state or in a wet pack package where the fibrin is maintained in a 100% relative humidity environment until end use.

It will be appreciated by those skilled in the art that while the invention has been described above in connection with particular embodiments the invention is not necessarily so limited and that numerous other embodiments, uses, modifications and departures from the embodiments, and uses may be made without departing from the inventive concepts.

We claim:

1. A method for making a drug eluting intravascular stent comprising the steps of:
    (a) providing a generally cylindrical stent body;
    (b) applying to the stent body a first layer which is a solid composite of polymer and therapeutic substance; and
    (c) applying as a second layer a layer of fibrin over the composite.

2. The method of claim 1 wherein the first layer is applied by the steps of:
    (a) applying to the stent body a solution which includes a solvent, a polymer dissolved in the solvent and a therapeutic substance dispersed in the solvent; and
    (b) evaporating the solvent to form a composite of polymer and therapeutic substance.

3. A method according to claim 2 wherein the solution is applied by spraying.

4. A method according to claim 2 wherein the solution is applied in a plurality of application and drying steps.

5. A method according to claim 2 wherein the ratio of therapeutic substance to dissolved polymer in the solution is varied in some of the plurality of application steps.

6. A method according to claim 2 wherein the polymer is a bioabsorbable polymer.

7. A method according to claim 6 wherein the polymer is selected from the group consisting of poly(L-lactic acid), poly(lactide-co-glycolide) and poly(hydroxybutyrate-co-valerate).

8. A method according to claim 2 wherein the polymer is a biostable polymer.

9. A method according to claim 8 wherein the polymer is selected from the group consisting of silicones, polyurethanes, polyesters, vinyl homopolymers and copolymers, acrylate homopolymers and copolymers, polyethers and cellulosics.

10. The method of claim 1 wherein the first layer is applied by the steps of:
    (a) applying to the stent body a solution which includes fibrinogen;
    (b) applying thrombin to the fibrinogen on the stent body to effect polymerization of the fibrinogen; and
    (c) applying a therapeutic substance to the fibrinogen as the fibrinogen is polymerizing.

11. The method of claim 1 wherein the first layer is applied by the steps of:
    (a) applying to the stent body a solution which includes fibrinogen and a dispersed therapeutic substance; and (b) applying thrombin to the fibrinogen on the stent body to effect polymerization of the fibrinogen.

12. A method according to claim 1 wherein the therapeutic substance is selected from the group consisting of glucocorticoids, heparin, hirudin, tocopherol, angiopeptin, aspirin, ACE inhibitors, growth factors, oligonucleotides, antiplatelet agents, anticoagulant agents, antimitotic agents, antioxidants, antimetabolite agents, and anti-inflammatory agents.

13. A method according to claim 1 wherein the fibrin is applied by molding a polymerization mixture of fibrinogen and thrombin onto the composite.

\* \* \* \* \*